US009022963B2

(12) United States Patent
Mobley

(10) Patent No.: US 9,022,963 B2
(45) Date of Patent: May 5, 2015

(54) NASAL SEPTAL SPLINT AND METHODS FOR USING SAME

(75) Inventor: Steven Ross Mobley, Park City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 128 days.

(21) Appl. No.: 13/453,676

(22) Filed: Apr. 23, 2012

(65) Prior Publication Data

US 2012/0271209 A1    Oct. 25, 2012

Related U.S. Application Data

(60) Provisional application No. 61/477,950, filed on Apr. 21, 2011.

(51) Int. Cl.
*A61F 5/00* (2006.01)
*A61F 13/00* (2006.01)

(52) U.S. Cl.
CPC . *A61F 13/00021* (2013.01); *A61F 2013/00476* (2013.01)

(58) Field of Classification Search
USPC ............... 128/846, 858; 606/204.15, 204.14; 602/41, 5; 2/174, 209, 215, 606
See application file for complete search history.

(56) References Cited

U.S. PATENT DOCUMENTS

| | | | |
|---|---|---|---|
| 4,402,314 A | 9/1983 | Goode | 128/76 C |
| 4,534,342 A * | 8/1985 | Pexa | 602/74 |
| D354,814 S | 1/1995 | Doyle | D24/140 |
| 5,931,799 A * | 8/1999 | Guastella et al. | 602/6 |
| D427,689 S | 7/2000 | Doyle | D24/190 |
| 6,186,965 B1 | 2/2001 | Patterson | 602/605 |
| 6,206,902 B1 * | 3/2001 | Morikane | 606/204.15 |
| 7,861,317 B2 * | 1/2011 | Beliveau | 2/9 |
| 2013/0276794 A1 * | 10/2013 | Morriss | 128/858 |

* cited by examiner

*Primary Examiner* — Michael A. Brown
(74) *Attorney, Agent, or Firm* — Ballard Spahr LLP

(57) ABSTRACT

A splint for use in stabilizing the nasal septum of a subject following the completion of a septoplasty procedure has a longitudinal axis and is formed of a substantially rigid sheet having a longitudinal length, an anterior end, and a posterior end. The sheet is labeled with a plurality of guide markings that guide a user in shaping the splint prior to implantation of the splint within a nasal passage of the subject.

24 Claims, 4 Drawing Sheets

NASAL SEPTAL SPLINT AND METHODS FOR USING SAME

CROSS-REFERENCE TO RELATED APPLICATIONS

This application claims priority to U.S. Provisional Patent Application No. 61/477,950, filed on Apr. 21, 2011, the entire disclosure of which is hereby incorporated by reference herein in its entirety.

FIELD OF THE INVENTION

This invention relates to splints for use in stabilizing the nasal septum of a subject following a septoplasty procedure and, more particularly, to asymmetrically folded splints that are configured for anterior positioning within the nasal passages of a subject following a septoplasty procedure.

BACKGROUND

Surgeries to correct problems in the nasal septum (septoplasties) are some of the most commonly performed outpatient surgical procedures. Nasal septal splints provide stability and support to the nasal septum following performance of a septoplasty procedure. Additionally, the septal splints prevent blood from accumulating within the nasal septum following the septoplasty procedure. Conventionally, one septal splint is placed on each side of the nasal septum, and the splints are secured into position using sutures through-and-through the splint material, thereby holding the splints in close apposition to the septum.

Conventional splints typically include pre-cut holes for receiving the sutures, as well as a pre-cut slit down the middle of the splint. These pre-cut holes are typically designed to receive sutures of any size and, thus, are often significantly larger than the sutures that are used to secure the splint to the nasal septum. Consequently, the pre-cut holes often permit undesired movement of the sutures that reduces the stability of the nasal septum following implantation of the splints. Additionally, the pre-cut holes often permit undesired infiltration (i.e., evagination through the holes) of mucosal tissue following suture-fixation of the splints. Therefore, in order to prevent these complications, conventional splints are typically secured to the nasal septum for no more than seven days, which is a sub-optimal length of time to allow for stable midline healing of the septum. Furthermore, the pre-cut slit in conventional splints extends down the middle of the splint and is primarily designed to allow the splint to collapse upon itself, thereby permitting easier removal of the splint past the nostril. However, this pre-cut slit is often in a sub-optimal position and can actually weaken the splint and render the splint less effective in accomplishing stable midline septal fixation. Additionally, due to the anatomy of the inferior floor of the human nose, such a symmetrical slit configuration often prevents medical practitioners from securing the splint within the anterior portion of the nose, an area that is often crucial to achieving stable, midline fixation. Moreover, conventional splints are typically formed of plastic that that has insufficient strength to accomplish a stable midline fixation to the nasal septum without securing the splint to the nasal spine. Additionally, the plastic used to form conventional splints loses its rigidity when further cutting of the splints is completed. Thus, changes made by medical practitioners to the design of a conventional splint typically result in performance disadvantages.

Accordingly, there is a need in the pertinent art for a splint that can be significantly more anteriorly positioned within the nose of the subject and can be used to accomplish a stable midline fixation to the nasal septum of the subject. There is a further need in the pertinent art for a nasal septal splint that can retain rigidity following cutting of the splint by a medical practitioner and that can be used to support a healing nasal septum for periods of two weeks or more.

SUMMARY

Described herein is a splint for use in stabilizing the nasal septum of a subject following the completion of a septoplasty procedure. In one aspect, the splint has a longitudinal axis and is formed of a substantially rigid sheet having a longitudinal length, an anterior end, and a posterior end. The sheet is bisected along its longitudinal length into a first portion and a second portion. Additionally, the sheet is labeled with a plurality of guide markings that are asymmetrically positioned along the longitudinal length of the sheet. The guide markings are in place to guide a user in shaping the splint prior to implantation of the splint within a nasal passage of the subject. Methods of preparing and using the splints are also disclosed.

BRIEF DESCRIPTION OF THE FIGURES

These and other features of the preferred embodiments of the invention will become more apparent in the detailed description in which reference is made to the appended drawings wherein:

FIG. 2 is a side view of the nose of the subject. FIG. 3 is a frontal view of the nose of the subject. FIG. 4 is a bottom view of the nose of the subject. FIG. 5 is a close-up view of FIG. 4 that displays the suturing of two splints to the nasal septum of the subject to accomplish a stable midline fixation.

DETAILED DESCRIPTION

Figure 1:
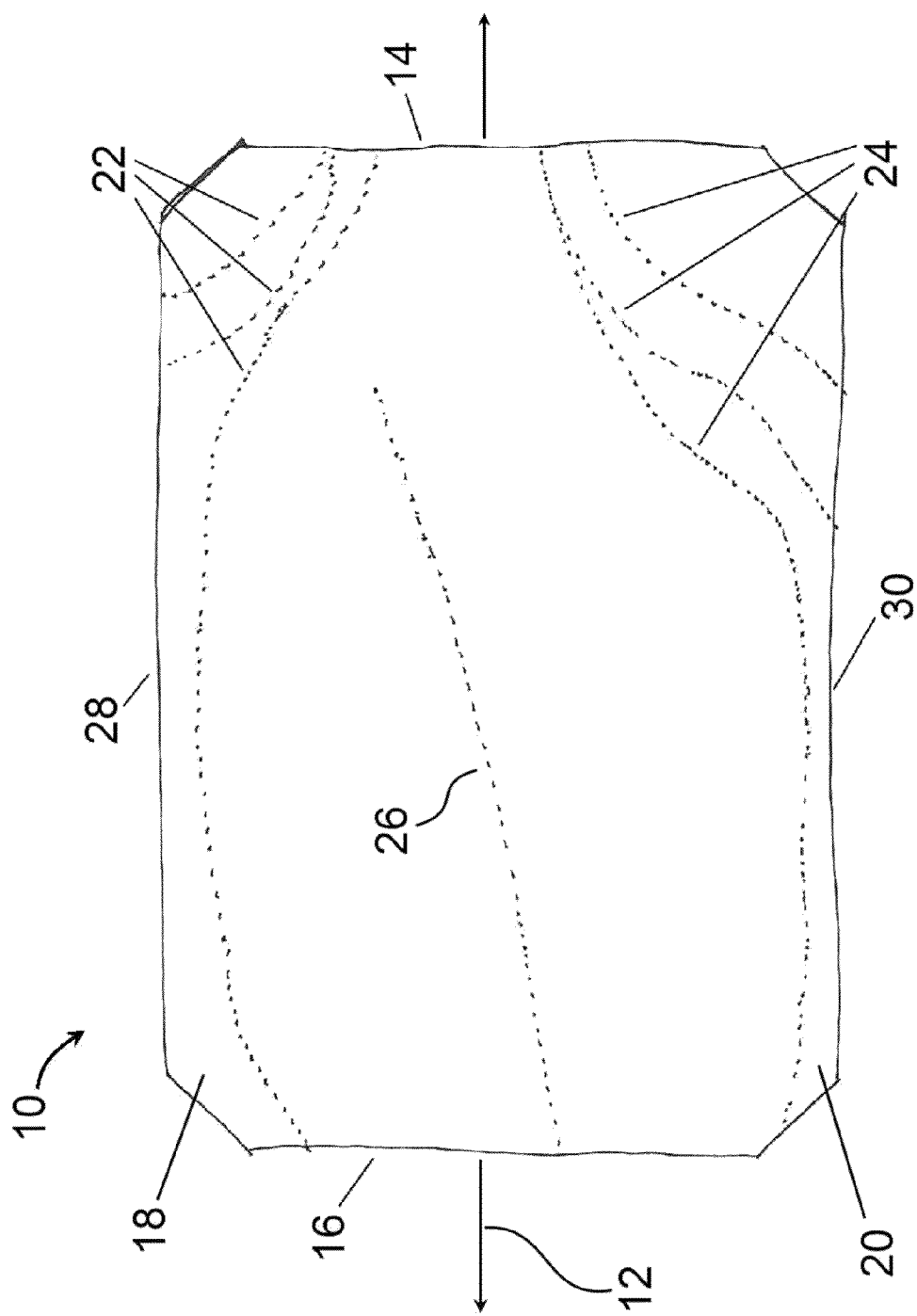
FIG. 1 is a top view of an exemplary splint having a plurality of guide markings, as described herein. The dashed lines depicted in FIG. 1 correspond to guide markings, as described herein.
Figure 2:
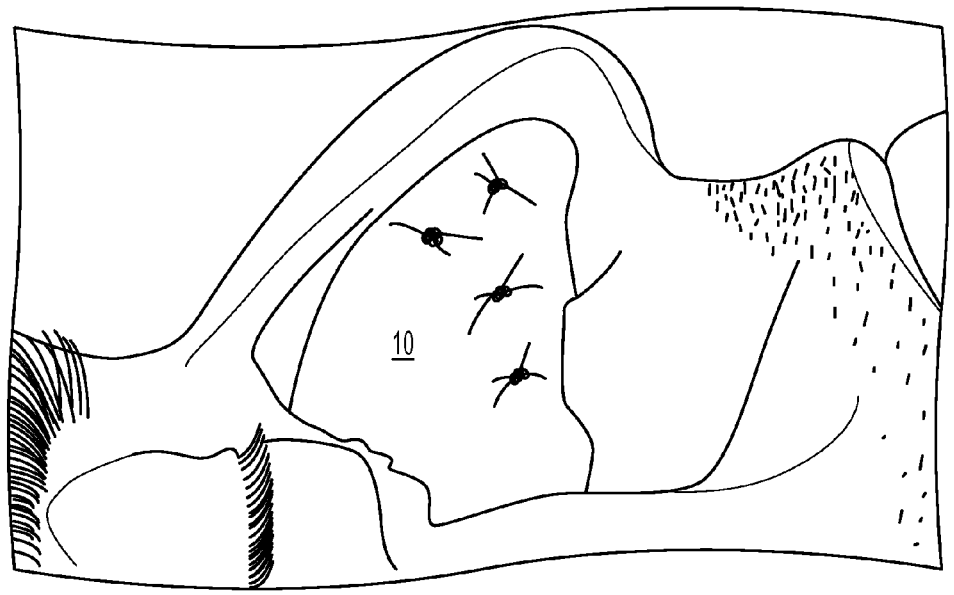
FIGS. 2-5 are images of septal splints secured to the nasal septum of a subject, as described herein.
Figure 3:

The present invention can be understood more readily by reference to the following detailed description, examples, drawings, and claims, and their previous and following description. However, before the present devices, systems, and/or methods are disclosed and described, it is to be understood that this invention is not limited to the specific devices, systems, and/or methods disclosed unless otherwise specified, and, as such, can, of course, vary. It is also to be understood that the terminology used herein is for the purpose of describing particular aspects only and is not intended to be limiting.

The following description of the invention is provided as an enabling teaching of the invention in its best, currently known embodiment. To this end, those skilled in the relevant art will recognize and appreciate that many changes can be made to the various aspects of the invention described herein, while still obtaining the beneficial results of the present invention. It will also be apparent that some of the desired benefits of the present invention can be obtained by selecting some of the features of the present invention without utilizing other features. Accordingly, those who work in the art will recognize that many modifications and adaptations to the present invention are possible and can even be desirable in certain circumstances and are a part of the present invention. Thus, the following description is provided as illustrative of the principles of the present invention and not in limitation thereof.

As used throughout, the singular forms "a," "an" and "the" include plural referents unless the context clearly dictates otherwise. Thus, for example, reference to "a splint" can include two or more such splints unless the context indicates otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, the terms "optional" or "optionally" mean that the subsequently described event or circumstance may or may not occur, and that the description includes instances where said event or circumstance occurs and instances where it does not.

The word "or" as used herein means any one member of a particular list and also includes any combination of members of that list.

In one embodiment, and with reference to FIGS. 1-5, the invention relates to a splint 10 for use in stabilizing a nasal septum of a subject following a septoplasty procedure. In one aspect, the splint 10 can comprise a substantially rigid sheet, which, optionally, can be formed from a polymeric material. In this aspect, the sheet (and, thus, the splint 10) can have a longitudinal axis 12, a longitudinal length (along the longitudinal axis of the splint), an anterior end 14, and a posterior end 16. It is contemplated that the splint 10 can be bisected along its longitudinal length into a first portion 18 and a second portion 20. It is further contemplated that the splint 10 can be labeled with a plurality of guide markings. In an additional aspect, the plurality of guide markings can be configured to guide a user, such as a surgeon or other medical practitioner, in shaping the splint 10 prior to implantation of the splint within a nasal passage of a subject. Optionally, in exemplary aspects, the splint 10 can be embossed to form the plurality of guide markings. In these aspects, it is contemplated that only a single surface of the splint 10 will be embossed to form the plurality of guide markings. In additional exemplary aspects, the splint 10 can be formed from a material having a first color, and the plurality of guide markings can optionally be indicated by, and correspond to, portions of the splint 10 having a color different from the first color. Thus, it is contemplated that the splint 10 can be a substantially smooth sheet, with the plurality of guide markings being indicated by one or more colors that contrast with the base color of the splint. In one aspect, the splint 10 can comprise plastic. In another aspect, it is contemplated that the splint 10 can be configured to retain its rigidity following completion of the cutting and re-sizing procedures described herein.

In exemplary aspects, it is contemplated that the splint 10 can be configured for implantation on a selected side of the nasal septum. Thus, it is contemplated that the splint 10 can be configured for implantation on the right side of the nasal septum. Alternatively, it is contemplated that the splint can be configured for implantation on the left side of the nasal septum. In use, it is contemplated that a first splint configured for implantation on the right side of the nasal septum can be used together with a second splint configured for implantation on the left side of the nasal septum to perform the surgical procedures described herein. As one will appreciate, the operative shape, and orientation of the guide markings, of a splint configured for implantation on the right side of the nasal septum can be different from the operative shape, and orientation of the guide markings, of a splint configured for implantation on the left side of the nasal septum. In exemplary aspects, it is contemplated that the operative shape of a first splint configured for implantation on the right side of the nasal septum can be substantially a mirror image of the operative shape of a second splint configured for implantation on the left side of the nasal septum. In these aspects, it is further contemplated that orientation and location of the guide markings of the first splint can be substantially a mirror image of the orientation and location of the guide markings of the second splint.

In one aspect, in addition to having a longitudinal length, the splint 10 can have an initial width and an initial thickness (measured prior to preparation of the splint for implantation into a subject). In this aspect, it is contemplated that the longitudinal length of the splint 10 can range from about 3.5 cm to about 5.5 cm, more preferably from about 4.0 cm to about 5.0 cm, and most preferably from about 4.25 cm to about 4.75 cm. It is further contemplated that the width of the splint 10 can range from about 2.0 cm to about 3.5 cm, more preferably from about 2.25 cm to about 3.25 cm, and most preferably from about 2.5 cm to about 3.0 cm. It is still further contemplated that the thickness of the splint 10 can range from about 0.25 mm to about 1.25 mm, more preferably from about 0.50 mm to about 1.00 mm, and most preferably from about 0.65 mm to about 0.85 mm.

In another aspect, and with reference to FIG. 1, the plurality of guide markings can comprise at least one first cutting location marking 22. In this aspect, the at least one first cutting location marking 22 can be positioned on the first portion 18 of the splint 10. It is contemplated that the at least one first cutting location marking 22 can extend from the anterior end 14 of the splint 10 along at least a portion of the longitudinal length of the splint. It is further contemplated that the at least one first cutting location marking 22 can comprise one, two, three, four, five, six, seven, eight, nine, ten, or more first cutting location markings.

In an additional aspect, the plurality of guide markings can comprise at least one second cutting location marking 24. In this aspect, the at least one second cutting location marking 24 can be positioned on the second portion 20 of the splint 10. It is contemplated that the at least one second cutting location marking 24 can extend from the anterior end 14 of the splint 10 along at least a portion of the longitudinal length of the splint. It is further contemplated that at least a portion of the at least one second cutting location marking 24 can be asymmetrical to the at least one first cutting location marking 22 along the longitudinal length of the splint 10. It is still further contemplated that the at least one second cutting location marking 24 can comprise one, two, three, four, five, six, seven, eight, nine, ten, or more second cutting location markings. In exemplary aspects, it is contemplated that the first and second cutting location markings 22, 24 can correspond to preferred locations for cutting the splint 10 prior to implantation of the splint within the nasal passage of the subject.

In another aspect, the plurality of guide markings can comprise a fold location marking 26. In this aspect, it is contemplated that the fold location marking 26 can extend substantially linearly from the posterior end 16 of the splint 10 along a portion of the longitudinal length of the splint. In one aspect, the fold location marking 26 can be angled relative to the longitudinal axis 12 of the splint 10. In this aspect, it is contemplated that the fold location marking 26 can extend from the posterior end 16 of the splint 10 through the second portion 20 of the splint and into the first portion 18 of the splint. In exemplary aspects, it is contemplated that the fold location marking 26 can correspond to a preferred location for folding the splint 10 such that the first and second portions 18, 20 of the splint are adjoined to shape the splint for complementary insertion within the nasal passage of the subject. In particular, it is contemplated that the fold location marking 26 can correspond to a preferred location for folding the splint 10 such that the splint is shaped for complementary positioning along the nasal floor of the subject and extending caudally up to the medial crural cartilages of the subject.

In a further aspect, the splint 10 can comprise a first side edge 28 and a second side edge 30. In this aspect, the first side edge 28 and the second side edge 30 can be positioned between and connected thereto the anterior end 14 and the posterior end 16 of the splint 10 along the longitudinal axis 12 of the splint. Optionally, as depicted in FIG. 1, it is contemplated that the side edges 28, 30 of the splint can intersect with the anterior and posterior ends 14, 16 of the splint 10 to define substantially rounded corners. In one aspect, the at least one first cutting location marking 22 can optionally comprise a first cutting location marking extending from the anterior end 14 of the splint to the first side edge 28. In this aspect, it is contemplated that the first cutting location marking extending from the anterior end 14 of the splint 10 to the first side edge 28 can be substantially arcuate. Optionally, in another aspect, the at least one first cutting location marking 22 can comprise a first cutting location marking extending from the anterior end 14 of the splint 10 to the posterior end of the splint. In this aspect, the first cutting location marking extending from the anterior end 14 of the splint 10 to the posterior end 16 of the splint can be substantially S-shaped.

Optionally, in an additional aspect, the at least one second cutting location marking 24 can comprise a second cutting location marking extending from the anterior end 14 of the splint 10 to the second side edge 30. In this aspect, it is contemplated that the second cutting location marking extending from the anterior end 14 of the splint 10 to the second side edge 30 can be substantially S-shaped. In a further aspect, the at least one second cutting location 24 can optionally comprise a second cutting location marking extending from the anterior end 14 of the splint 10 to the posterior end 16 of the splint. In this aspect, it is contemplated that the second cutting location marking 24 extending from the anterior end 14 of the splint 10 to the posterior end 16 of the splint can be substantially S-shaped.

In a further aspect, it is contemplated that one or more splints 10 can be provided in a kit. In this aspect, it is contemplated that the one or more splints 10 of the kit can comprise splints configured for implantation on the right side of the nasal septum and corresponding splints configured for implantation on the left side of the nasal septum. It is further contemplated that the kit can comprise additional elements used during preparation and/or implantation of the splints, as described herein. It is still further contemplated that the kit can include text or markings indicative of the relative size of the splints in the kit and/or the shapes and orientation of the guide markings of the splints in the kit.

It is contemplated that a user, such as an attending surgeon or other medical practitioner, can customize the shape of each splint as necessary for each subject. Thus, it is contemplated that the user can selectively determine which of the guide markings should be used in appropriately shaping the splint for insertion within the nasal passage of the subject. For example, it is contemplated that the first cutting location marking can be selectively chosen for each subject as necessary to conform the shape of the splint to the shape of the anterior portion of the nose of the subject.

In exemplary aspects, it is contemplated that the splint can be cut along the guide markings as necessary to prepare the splint for positioning within an anterior portion of the nasal passage of the subject. For example, it is contemplated that, upon insertion within the nasal passage of the subject, the splint can be secured posteriorly to the outer surface of the columella of the subject. In one exemplary aspect, the splint can be secured just behind the outer surface of the columella, just along the vestibular lining and over the outer edges of the medial crural cartilages. Thus, it is further contemplated that, after the splint is secured, the splint can be posteriorly spaced from the columella by less than 4 mm, and more preferably, by less than about 2-3 mm.

In an exemplary aspect, the splint can be coated with one or more biocompatible coatings for easing movement of the splint into, out of, and/or within a nasal passage of the subject. In this aspect, it is contemplated that the one or more biocompatible coatings can comprise a film, such as, for example and without limitation, a biofilm. It is further contemplated that the one or more biocompatible coatings can comprise one or more non-degradable polymers, such as, for example and without limitation, poly(ethylene glycol) (PEG). It is further contemplated that the one or more biocompatible coatings can be substantially non-adhering and can, therefore, be configured to resist adherence to the mucosal membranes within the nasal passages of the subject. For example, the splint can be made of or coated with a clear, medical-grade fluoroplastic that is flexible and non-adherent. It is still further contemplated that the one or more biocompatible coatings can be configured to reduce irritation of the mucosal membranes within the nose of the subject during movement of the splint. In another exemplary aspect, the splint can include flesh-colored or decorative materials of construction and/or coatings, with the entire compound splint being manufactured of water-resistant materials.

In an exemplary aspect, the splint can be coated or impregnated with one or more biocompatible coatings, such as, for example and without limitation, antibiotics, antivirals and/or anti-clotting compounds.

Optionally, in another aspect, the splint can be coated with a biocompatible coating that is configured to resist the build up of dry nasal crusts. In one exemplary aspect, it is contemplated that the splint can be coated on a first side with a conventional topical coating and can be coated on a second side with a biocompatible coating that is configured to resist the build up of dry nasal crusts.

In use, and with reference to FIGS. 2-5, the disclosed splints can be employed in a method for reconstructing the nose of the subject. In one aspect, the method for reconstructing the nose of the subject can comprise providing a first splint and a second splint, as described herein. In another aspect, the method for reconstructing the nose of the subject can comprise cutting the first and second splints along respective first cutting location markings positioned on the first portion of each respective splint. In an additional aspect, the method for reconstructing the nose of the subject can comprise cutting the first and second splints along respective second cutting location markings positioned on the second portion of each respective splint. In a further aspect, the method for reconstructing the nose of the subject can comprise folding the first and second splints along their respective fold location markings such that the first and second portions of each respective splint approach one another to place each respective splint in an operative configuration. In this aspect, it is contemplated that, in the operative configuration, each respective splint can be shaped for complementary insertion within the nasal passage of the subject. It is further contemplated that, in the operative configuration, each respective splint can be folded such that the majority of the material forming the splint is configured for positioning proximate the anterior portion of the nose of the subject.

In another aspect, while the first splint is in the operative configuration, the method for reconstructing the nose of the subject can comprise inserting the first splint into a first nasal passage of the subject. In still another aspect, while the second splint is in the operative configuration, the method for reconstructing the nose of the subject can comprise inserting the second splint into a second nasal passage of the subject. In yet another aspect, the method for reconstructing the nose of the subject can comprise securing the first splint to the second splint through the septum of the nose of the subject.

Figure 4:
Figure 5:

It is contemplated that the step of securing the first splint to the second splint can further comprise securing the first splint to the second splint through the septum of the nose of the subject using at least one conventional suture, which is passed through each respective splint. In exemplary aspects, as shown in FIGS. 4 and 5, the sutures can provide a stable midline fixation of the first and second splints to the septum of the subject. In this aspect, it is contemplated that the first splint and second splint can be secured within the nasal passages of the subject such that the septum of the nose of the subject is squeezed between the first splint and the second splint, thereby improving the stability of the septum. It is still further contemplated that the first splint and the second splint can be secured to the septum of the nose of the subject as described herein for at least two weeks. However, it is contemplated that the splints can be secured as described herein for any period of time necessary to adequately reconstruct the nose of the subject.

It is contemplated that the at least one suture that is passed through the respective splints can be applied between the splints using conventional methods and surgical tools, such as, for example and without limitation, conventional surgical needles. Thus, it is further contemplated that the at least one suture can pass through the respective splints such that the sutures are firmly positioned within the splints and movement of the sutures is minimized. In these aspects, it is contemplated that, as compared with known methods, the elimination of pre-formed holes, which create gaps between the sutures and the boundaries of each hole, can significantly reduce the invasion of the mucus membrane of the subject into the splints.

It is contemplated that the methods disclosed herein can be accomplished using conventional surgical tools as are commonly known in the art. It is further contemplated that the sutures employed in the disclosed methods can be conventional sutures as are commonly known in the art. In exemplary aspects, it is contemplated that the sutures employed in the disclosed methods can be 4-0 (about 0.15 mm diameter) black nylon sutures that are applied using a conventional FSL (For skin-larger) needle.

Also disclosed is a method for preparing the splint for implantation within the nasal passage of the subject. In one aspect, the method for preparing the splint for implantation comprises providing a splint as described herein. In another aspect, the method for preparing the splint for implantation comprises cutting the splint along a first cutting location marking positioned on the first portion of the splint. In an additional aspect, the method for preparing the splint for implantation comprises cutting the splint along a second cutting location marking positioned on the second portion of the splint. In a further aspect, the method for preparing the splint for implantation comprises folding the splint along the fold location marking such that the first and second portions of the splint approach one another to place the splint in the operative configuration.

In use, it is contemplated that, because the disclosed splints can be anteriorly positioned within the nasal passage of a subject along the nasal floor and within about 2-3 mm of the columella as described herein, it is unnecessary to secure the nasal septum to the nasal spine. Instead, a described herein, splints are inserted and anteriorly positioned on both sides of the nasal septum, and the attending surgeon can sew through-and-through the splints using conventional sutures. After sewing through-and-through the splints, the surgeon can then tighten the knot associated with the sutures, thereby tightening the splints against the septum in a midline position. Thus, it is contemplated that the disclosed splints and methods can be employed to decrease operating room time and surgical complexity while providing an improved, more stable, and more anterior midline fixation that can be left secured within a subject for two weeks or more without the negative consequences associated with known splints.

Although several embodiments of the invention have been disclosed in the foregoing specification, it is understood by those skilled in the art that many modifications and other embodiments of the invention will come to mind to which the invention pertains, having the benefit of the teaching presented in the foregoing description and associated drawings. It is thus understood that the invention is not limited to the specific embodiments disclosed hereinabove, and that many modifications and other embodiments are intended to be included within the scope of the appended claims. Moreover, although specific terms are employed herein, as well as in the claims which follow, they are used only in a generic and descriptive sense, and not for the purposes of limiting the described invention, nor the claims which follow.

What is claimed is:

1. A splint having a longitudinal axis, a longitudinal length, an anterior end, and a posterior end opposed from the anterior end, the splint being bisected along its longitudinal length into a first portion and a second portion, wherein the splint is labeled with a plurality of guide markings for guiding a user in shaping the splint prior to implantation within a nasal passage of a subject, the plurality of guide markings comprising:

at least one first cutting location marking positioned on the first portion of the splint, the at least one first cutting location marking extending from the anterior end of the splint along at least a portion of the longitudinal length of the splint, wherein the at least one first cutting location marking comprises a first cutting location marking extending from the anterior end of the splint to the posterior end of the splint;

at least one second cutting location marking positioned on the second portion of the splint, the at least one second cutting location marking extending from the anterior end of the splint along at least a portion of the longitudinal length of the splint, wherein at least a portion of the at least one second cutting location marking is asymmetrical to the at least one first cutting location marking along the longitudinal length of the splint; and a fold location marking extending substantially linearly from the posterior end of the splint along a portion of the longitudinal length of the splint, wherein the first and second cutting location markings correspond to preferred locations for cutting the splint, and wherein the fold location marking corresponds to a preferred location for folding the splint, wherein, following cutting of the splint at a first cutting location marking and a second cutting location marking and folding of the splint at the fold location marking, the first and second portions of the splint are configured to approach one another to place the splint in an operative position, and wherein, in the operative position, the splint is configured for complementary insertion within the nasal passage of the subject.

2. The splint of claim 1, wherein the fold location marking is angled relative to the longitudinal axis of the splint.

3. The splint of claim 2, wherein the fold location marking extends from the posterior end of the splint through the second portion of the splint and into the first portion of the splint.

4. The splint of claim 1, wherein the splint is embossed to form the plurality of guide markings.

5. The splint of claim 1, wherein the first cutting location marking extending from the anterior end of the splint to the posterior end of the splint is substantially S-shaped.

6. The splint of claim 1, wherein the at least one second cutting location marking comprises a second cutting location marking extending from the anterior end of the splint to the second side edge.

7. The splint of claim 6, wherein the second cutting location marking extending from the anterior end of the splint to the first side edge is substantially S-shaped.

8. The splint of claim 1, wherein the at least one second cutting location marking comprises a second cutting location marking extending from the anterior end of the splint to the posterior end of the splint.

9. The splint of claim 8, wherein the second cutting location marking extending from the anterior end of the splint to the posterior end of the splint is substantially S-shaped.

10. The splint of claim 1, wherein at least a portion of the splint is coated with one or more biocompatible coatings configured to ease movement of the splint within the nasal passage of the subject.

11. A method for reconstructing a nose of a subject, the nose having a septum, the method comprising:
providing a first splint and a second splint, each splint having a longitudinal axis, a longitudinal length, an anterior end, and a posterior end, the splint being bisected along its longitudinal length into a first portion and a second portion, wherein the splint is labeled with a plurality of guide markings configured to guide a user in shaping the splint prior to implantation within a nasal passage of the subject, the plurality of guide markings comprising:
a plurality of cutting location markings extending from the anterior end of the splint along at least a portion of the longitudinal length of the splint, the plurality of cutting location markings being asymmetrically positioned relative to the longitudinal axis of the splint; and
a fold location marking extending from the posterior end of the splint along a portion of the longitudinal length of the splint,
cutting the first and second splints along respective first cutting location markings positioned on the first portion of each respective splint, the first cutting location markings extending from the anterior end of each respective splint along at least a portion of the longitudinal length of each respective splint;
cutting the first and second splints along respective second cutting location markings positioned on the second portion of each respective splint, the second cutting location markings extending from the anterior end of each respective splint along at least a portion of the longitudinal length of each respective splint;
folding the first and second splints along their respective fold location markings such that the first and second portions of each respective splint approach one another to place each respective splint in an operative configuration, wherein, in the operative configuration, each respective splint is shaped for complementary insertion within a nasal passage of the subject;
inserting the first splint into a first nasal passage of the subject while the first splint is in the operative configuration;
inserting the second splint into a second nasal passage of the subject while the second splint is in the operative configuration; and
securing the first splint to the second splint through the septum of the nose of the subject.

12. The method of claim 11, wherein the first splint and the second splint are formed from a polymeric material.

13. The method of claim 11, wherein at least a portion of the first splint is coated with one or more biocompatible coatings configured to ease movement of the first splint within the first nasal passage of the subject, and wherein at least a portion of the second splint is coated with one or more biocompatible coatings configured to ease movement of the second splint within the second nasal passage of the subject.

14. A method for preparing a splint for implantation within a nasal passage of a subject, the method comprising:
providing a splint having a longitudinal axis, a longitudinal length, an anterior end, and a posterior end, the splint being bisected along its longitudinal length into a first portion and a second portion, wherein the splint is labeled with a plurality of guide markings for guiding a user in shaping the splint prior to implantation within a nasal passage of the subject, the plurality of guide markings comprising:
a plurality of cutting location markings extending from the anterior end of the splint along at least a portion of the longitudinal length of the splint, the plurality of cutting location markings being asymmetrically positioned relative to the longitudinal axis of the splint; and
a fold location marking extending from the posterior end of the splint along a portion of the longitudinal length of the splint,
cutting the splint along a first cutting location marking positioned on the first portion of the splint, the first cutting location marking extending from the anterior end of the splint along at least a portion of the longitudinal length of the splint;
cutting the splint along a second cutting location marking positioned on the second portion of the splint, the second cutting location marking extending from the anterior end of the splint along at least a portion of the longitudinal length of the splint; and
folding the splint along the fold location marking such that the first and second portions of the splint approach one another to place the splint in an operative configuration, wherein, in the operative configuration, the splint is shaped for complementary insertion within the nasal passage of the subject.

15. The method of claim 14, wherein the splint is formed from a polymeric material.

16. The method of claim 14, wherein at least a portion of the splint is coated with one or more biocompatible coatings for easing movement of the splint within the nasal passage of the subject.

17. A splint having a longitudinal axis, a longitudinal length, an anterior end, a posterior end opposed from the anterior end, a first side edge, and a second side edge, the first side edge and the second side edge positioned between and connected thereto the anterior end and the posterior end of the splint along the longitudinal axis of the splint, the sheet being bisected along its longitudinal length into a first portion and a second portion, wherein the splint is labeled with a plurality of guide markings for guiding a user in shaping the splint prior to implantation within a nasal passage of a subject, the plurality of guide markings comprising:

- at least one first cutting location marking positioned on the first portion of the splint, the at least one first cutting location marking extending from the anterior end of the splint along at least a portion of the longitudinal length of the splint, wherein the at least one first cutting location marking comprises a first cutting location marking extending from the anterior end of the splint to the first side edge;
- at least one second cutting location marking positioned on the second portion of the splint, the at least one second cutting location marking extending from the anterior end of the splint along at least a portion of the longitudinal length of the splint, wherein at least a portion of the at least one second cutting location marking is asymmetrical to the at least one first cutting location marking along the longitudinal length of the splint, and wherein the at least one second cutting location marking comprises a second cutting location marking extending from the anterior end of the splint to the posterior end of the splint; and
- a fold location marking extending substantially linearly from the posterior end of the splint along a portion of the longitudinal length of the splint,
- wherein the first and second cutting location markings correspond to preferred locations for cutting the splint, and wherein the fold location marking corresponds to a preferred location for folding the splint, wherein, following cutting of the splint at a first cutting location marking and a second cutting location marking and folding of the splint at the fold location marking, the first and second portions of the splint are configured to approach one another to place the splint in an operative position, and wherein, in the operative position, the splint is configured for complementary insertion within the nasal passage of the subject.

18. The splint of claim 17, wherein the fold location marking is angled relative to the longitudinal axis of the splint.

19. The splint of claim 18, wherein the fold location marking extends from the posterior end of the splint through the second portion of the splint and into the first portion of the splint.

20. The splint of claim 17, wherein the splint is embossed to form the plurality of guide markings.

21. The splint of claim 17, wherein the first cutting location marking extending from the anterior end of the splint to the first side edge is substantially arcuate.

22. The splint of claim 17, wherein the at least one second cutting location marking comprises an additional second cutting location marking extending from the anterior end of the splint to the second side edge.

23. The splint of claim 22, wherein the additional second cutting location marking extending from the anterior end of the splint to the first side edge is substantially S-shaped.

24. The splint of claim 17, wherein the second cutting location marking extending from the anterior end of the splint to the posterior end of the sheet is substantially S-shaped.

* * * * *